US00PP25614P3

(12) United States Plant Patent
Egger

(10) Patent No.: US PP25,614 P3
(45) Date of Patent: Jun. 2, 2015

(54) ***AGASTACHE* PLANT NAMED 'KUDOS AMBROSIA'**

(50) Latin Name: ***Agastache* hybrid**
Varietal Denomination: Kudos Ambrosia

(71) Applicant: Terra Nova Nurseries, Inc., Canby, OR (US)

(72) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 184 days.

(21) Appl. No.: 13/986,945

(22) Filed: Jun. 18, 2013

(65) Prior Publication Data

US 2014/0373234 P1 Dec. 18, 2014

(51) Int. Cl.
*A01H 5/02* (2006.01)

(52) U.S. Cl.
USPC ..... Plt./399

(58) Field of Classification Search
USPC ..... Plt./399
See application file for complete search history.

(56) References Cited

PUBLICATIONS

Internet Retrieval on http://www.greenhousegrower.com/varieties/terra-nova-nuseries for agastache cultivar named 'Kudo's Ambrosia'. 2 pages total.*

* cited by examiner

*Primary Examiner* — Susan McCormick Ewoldt
(74) *Attorney, Agent, or Firm* — Klarquist Sparkman, LLP

(57) ABSTRACT

A new and distinct form of *Agastache* plant characterized by orange flower buds open to pink flowers in large inflorescences, a long bloom time, a very short, compact habit, good winter hardiness, and excellent vigor.

1 Drawing Sheet

Botanical denomination: *Agastache* hybrid.
Variety designation: 'Kudos Ambrosia'.

BACKGROUND OF THE INVENTION

The present invention relates to a new and distinct cultivar of *Agastache*, given the name, 'Kudos Ambrosia'. *Agastache* is in the family Lamiaceae. This new variety is one of several selections of new *Agastache* using hardy and dwarf *Agastache* species in the breeding lines to provide hardiness and compactness. The new cultivar is a selection from the cross between the proprietary seedlings *Agastache* S-1, as the seed parent, and *Agastache* 52-1, as the pollen parent. The new cultivar was selected for its compact habit, hardiness, and bicolor pink and orange flowers.

Compared to the seed parent, *Agastache* S-1, the new cultivar is shorter and hardier.

Compared to the pollen parent, *Agastache* 52-1, the new cultivar has larger orange buds to pink flowers rather than small light pink flowers.

Compared to *Agastache* 'Kiegabi', U.S. Plant Pat. No. 16,023 (sold as Salmon and Pink), the new cultivar is more compact, hardier, with the orange flower buds to pink flowers rather than salmon and pink flowers.

This plant exhibits the following characteristics that make it unique:

1. orange flower buds open to pink flowers in large inflorescences,
2. a long bloom time,
3. a very short, compact habit,
4. good winter hardiness,
5. and excellent vigor.

The new variety has been reproduced only by asexual propagation (stem cuttings and micropropagation using apical buds and nodes). Each of the progeny exhibits identical characteristics to the original plant. Asexual propagation by stem cuttings and micropropagation using apical buds and nodes as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows the new cultivar grown in a one gallon container in full sun in Canby, Oreg.

FIG. 2 shows nine-month-old *Agastache* 'Kudos Ambrosia' growing in the field in mid summer in Canby, Oreg.

DETAILED PLANT DESCRIPTION

The following is a detailed description of the new *Agastache* cultivar based on observations of 1-year-old specimens in late May growing in full sun in gallon containers in Canby, Oreg. Canby is Zone 8 on the USDA Hardiness map. Temperatures range from a high of 95° F. in August to an average of 32° F. in January. Normal rainfall in Canby is 42.8 inches per year. The color descriptions are all based on The Royal Horticultural Society Colour Chart, $5^{th}$ edition.

Plant:

*Form.*—Upright.

*Type.*—Herbaceous perennial.

*Cold hardiness.*—USDA Zone 6-10.

*Size.*—Grows to 36 cm wide and 44 cm tall to the top of the flowers.

*Vigor.*—Excellent.

*Branching.*—About 12 main stems from the base, these branch at every node.

*Stem.*—Square in cross section, grows to 4 mm wide and 37 cm tall to the first flower, pubescent, internodes range from 3 to 5 cm long, Yellow Green 147B.

*Roots.*—White 155B, fibrous, plants root easily from stem tip cuttings.

Leaf:

*Type.*—Simple.

*Arrangement.*—Opposite.

*Shape.*—Ovate.

*Venation.*—Pinnate.

*Margins.*—Coarsely serrate.

*Apex.*—Acute.

*Base.*—Cuneate to cordate.

*Blade size.*—Grows to 30 mm long and 26 mm wide.

*Surface texture.*—Pubescent on both sides.

*Petiole description.*—12 mm long and 1.5 mm wide, pubescent, Yellow Green 147B.

*Leaf color.*—Top side Yellow Green 147A, including vein; bottom side closest to Yellow Green 147B including vein.

*Fragrance.*—Aromatic.

Inflorescence:

*Type.*—Terminal spike with up to 8 whorls.

*Number of flowers.*—Up to 150 per spike.

*Size of inflorescence.*—Grows to 14 cm tall and 6 cm wide.

*Peduncle.*—Grows to 4.5 cm tall and 2.5 mm wide, pubescent, Yellow Green 147B.

*Pedicel.*—Grows to 2 mm long, pubescent, Purple N77C.

*Bloom period.*—Late May through frost in Canby, Oreg.

Flower bud:

*Size.*—26 mm long and 7 mm wide at the widest point prior to opening.

*Description.*—Tubular.

*Surface texture.*—Pubescent.

*Color.*—Orange Red 35B.

Flower:

*Type.*—Zygomorphic.

*Shape.*—Bilabiate, tubular.

*Size.*—32 mm long and 12 mm wide.

*Corolla description.*—30 mm long and spreads to 12 mm wide; color Greyed Purple 186C outside, Red Purple 72C inside; glabrous inside and pubescent outside, tube 20 mm long and 1.5 mm to 6 mm wide; 2 upper lobes joined 5 mm long and 5 mm wide, each ovate, tips obtuse, margin irregularly denticulate on top to entire on sides; three lower lobes, two spreading sideways and curve out slightly, each 3 mm deep and 5 mm wide, tip obtuse, margin entire; bottom lobe, reflexed, broadly obovate, notched at the tip, margin irregularly incised, 10.5 mm wide and 5 mm deep.

*Calyx description.*—Campanulate, 8 mm long and 4 mm wide, pubescent outside and glabrous inside, 5 lobed, lobes ovate, 2 mm long, entire, acuminate, Purple N77A outside, inside Yellow Green 147B on tube to Purple N77B on lobes.

*Pistil description.*—32 mm long, ovary 1 mm long, Yellow Green 147A, style 29 mm long, White NN155D blending to top 4 mm where Red Purple 72C, stigma two-parted, 1 mm deep, Red Purple 72A.

*Stamen description.*—4 in number, paired and exerted, top two 9 mm long and bottom two 7 mm long, filaments Red Purple 72C, anthers 1 mm long, Purple N77C, pollen none, male sterile.

*Fragrance.*—Aromatic.

*Lastingness.*—A spike blooms for about 4 weeks on the plant.

Fruit/seed: 4 nutlets, 1 mm long, ovoid, Black 202A.

Pests and diseases: The new cultivar is typical to the genus. No known resistances to pests or diseases. No problems have been found in Canby, Oreg.

I claim:

1. A new and distinct form of *Agastache* plant substantially as shown and described.

* * * * *

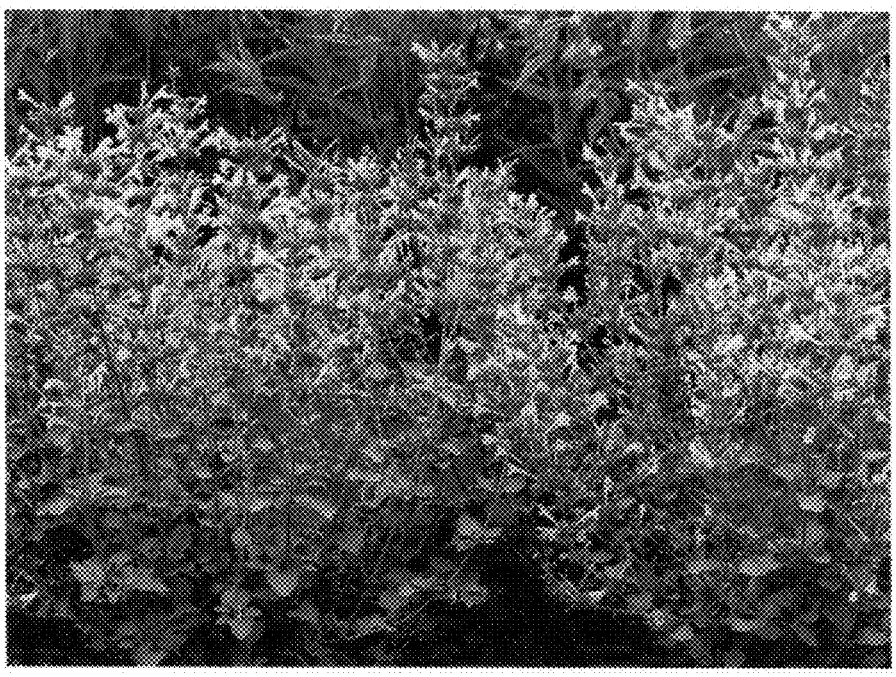

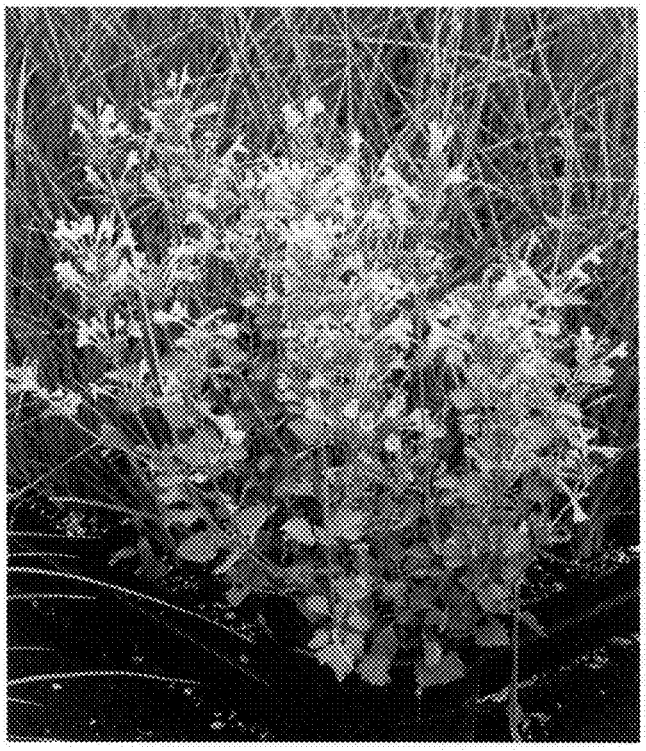
FIG. 1 above, FIG. 2 below